(12) United States Patent
Moinet et al.

(10) Patent No.: US 7,897,644 B2
(45) Date of Patent: Mar. 1, 2011

(54) USE OF 4-OXOBUTANOIC ACID DERIVATIVES IN THE TREATMENT OF INFLAMMATION

(75) Inventors: Gérard Moinet, Orsay (FR); Dominique Marais, Meulan (FR); Philippe Maizeray, Ledeville (FR)

(73) Assignee: Merck Patent Gesellschaft mit Beschrankter Haftung, Darmstadt (DE)

( * ) Notice: Subject to any disclaimer, the term of this patent is extended or adjusted under 35 U.S.C. 154(b) by 1997 days.

(21) Appl. No.: 10/497,491

(22) PCT Filed: Nov. 6, 2002

(86) PCT No.: PCT/EP02/12357
§ 371 (c)(1),
(2), (4) Date: Jun. 3, 2004

(87) PCT Pub. No.: WO03/047561
PCT Pub. Date: Jun. 12, 2003

(65) Prior Publication Data
US 2005/0014768 A1 Jan. 20, 2005

(30) Foreign Application Priority Data
Dec. 3, 2001 (FR) ...................................... 01 15601

(51) Int. Cl.
*A01N 37/00* (2006.01)
*A61K 31/185* (2006.01)
(52) U.S. Cl. ...................................................... 514/576
(58) Field of Classification Search .................. 514/256, 514/576
See application file for complete search history.

(56) References Cited

U.S. PATENT DOCUMENTS

| | | | |
|---|---|---|---|
| 3,784,701 A * | 1/1974 | Tomcufcik et al. | 514/570 |
| 5,886,024 A | 3/1999 | Kluender et al. | |
| 6,060,250 A * | 5/2000 | Lal et al. | 435/6 |
| 6,143,787 A * | 11/2000 | Moinet et al. | 514/568 |
| 6,262,060 B1 | 7/2001 | Bedoya-Zurita et al. | |
| 6,350,885 B1 | 2/2002 | OBrien et al. | |

FOREIGN PATENT DOCUMENTS

| | | | |
|---|---|---|---|
| WO | WO 97/17317 | * | 5/1997 |
| WO | WO 9743237 | | 11/1997 |
| WO | WO 9807681 | | 2/1998 |
| WO | WO 9952876 | | 10/1999 |
| WO | WO 0006560 | | 2/2000 |
| WO | WO 0067752 | | 11/2000 |

OTHER PUBLICATIONS

Krendel, D. A., Vascular inflammation in proximal diabetic neuropathy, Journal of Neruology (1998) 245: 748.*
Database WPI, Week 2000207, Derwent Publications Ltd., London, GB; AN 2001-570602, abstract & Database Caplus 'Online! Chemical Abstracts Service, Columbus Ohio, US voir les "IT" & WO 01 62295 A Aug. 30, 2001.
Galardy R E et al: "Inhibition of Carboxypeptidase A by Aldehyde and Ketone Substrate Analogues" Biochemistry, American Chemical Society. Easton, PA, vol. 23, No. 9, Apr. 24, 1984, pp. 2083-2087, ISSN: 0006-2960, the whole document.
Patent Abstracts of Japan & JP 59 144717 (Microbial Chem. Res. Found.), Aug. 18, 1984, abstract.
Database Caplus 'Online! Chemical Abstracts Service, Columbus OH, retrieved from STN, accession No. 1994: 244198, Database accession No. 120:244198 abstract & Fuji et al: "New preparation methods for optically active anti-inflammatory agents" Ikagaku Oyo Kenkyu Zaidan Kenkyu Hokoku, vol. 11, 1992, pp. 191-196.

* cited by examiner

*Primary Examiner* — Frederick Krass
*Assistant Examiner* — Benjamin Packard
(74) *Attorney, Agent, or Firm* — Millen, White, Zelano & Branigan, P.C.

(57) ABSTRACT

The present invention relates to the use of a 4-oxobutanoic acid derivative for the preparation of a pharmaceutical composition for treating inflammation.

12 Claims, No Drawings

USE OF 4-OXOBUTANOIC ACID DERIVATIVES IN THE TREATMENT OF INFLAMMATION

The present invention relates to the use of a 4-oxobutanoic acid derivative for the preparation of a pharmaceutical composition for treating inflammation.

4-Oxobutanoic acid derivatives have already been described in patent application WO 98/07681 as antidiabetic agents and more particularly for treating non-insulin-dependent diabetes.

Thus, the present patent application relates firstly to the use of at least one 4-oxobutanoic acid derivative conforming to the general formula (I) for the preparation of a medicament for treating inflammation.

The compound of the formula (I) is defined as follows:

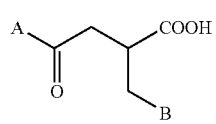

in which the groups A and B are chosen, independently of each other, from:
- a mono-, bi- or tricyclic aryl group containing from 6 to 14 carbon atoms;
- a heteroaromatic group chosen from pyridyl, pyrimidyl, pyrrolyl, furyl and thienyl groups;
- an alkyl group containing from 1 to 14 carbon atoms;
- a cycloalkyl group containing from 5 to 8 carbon atoms;
- a saturated heterocyclic group chosen from tetrahydrofuryl, tetra-hydropyranyl, piperidyl and pyrrolidinyl groups;
- where the groups A and B may carry from 1 to 3 substituents chosen from a $C_1$-$C_6$ alkyl group, a $C_1$-$C_6$ alkoxy group, a $C_6$-$C_{14}$ aryl group, a heteroaryl group chosen from pyridyl, pyrimidyl, pyrrolyl, furyl and thienyl, a ($C_6$-$C_{14}$)aryl($C_1$-$C_6$) alkyl group, a ($C_6$-$C_{14}$)aryl($C_1$-$C_6$)alkyl($C_6$-$C_{14}$)aryl group, a halogen or a tri-fluoromethyl, trifluoromethoxy, cyano, hydroxyl, nitro, amino, carboxyl, ($C_1$-$C_6$)-alkoxycarbonyl, carbamoyl, ($C_1$-$C_6$)alkylsulfonyl, sulfoamino, ($C_1$-$C_6$)alkylsulfonyl-amino, sulfamoyl or ($C_1$-$C_6$)alkylcarbonylamino group;
- or two of the substituents form a methylenedioxy group, a solvate thereof or a salt of this acid.

In a preferred embodiment of the invention, the 4-oxobutanoic acids are those of the formula (I) in which A and B are chosen from aryl groups.

Examples of aryl groups that may be mentioned include phenyl, α-naphthyl, β-naphthyl and fluorenyl groups.

The $C_1$-$C_6$ alkyl groups may be linear or branched. Examples that may be mentioned include methyl, ethyl, propyl, isopropyl, butyl, isobutyl, tert-butyl and pentyl groups.

The $C_1$-$C_6$ alkoxy groups may also be linear or branched.

Examples that may be mentioned include methoxy, ethoxy, propoxy, isopropoxy, butoxy and isobutoxy groups.

The halogens may be chosen from fluorine, chlorine, bromine and iodine.

The present invention also includes the tautomeric forms of the compounds of the general formula (I), the enantiomers, diastereoisomers and epimers of these compounds, and also the solvates thereof.

Examples of salts of the compounds of the general formula (I) include pharmacologically acceptable salts, such as the sodium salts, potassium salts, magnesium salts, calcium salts, amine salts and other salts of the same type (aluminium, iron, bismuth, etc.).

In a preferred embodiment, the 4-oxobutanoic acids are chosen from:
2-benzyl-4-(4-methoxyphenyl)4-oxobutanoic acid
2-benzyl-4-(4-fluorophenyl)-4-oxobutanoic acid
2-cyclohexylmethyl-4-(4-methoxyphenyl)4-oxobutanoic acid
2-benzyl-4-phenyl-4-oxobutanoic acid
2-(β-naphthylmethyl)-4-phenyl-4-oxobutanoic acid
2-benzyl-4-(β-naphthyl)-4-oxobutanoic acid
2-[(4-chlorophenyl)methyl]-4-(4-methoxyphenyl)-4-oxobutanoic acid
2-benzyl-4-(4-methylphenyl)-4-oxobutanoic acid
4-(4-fluorophenyl)-2-[(4-methoxyphenyl)methyl]-4-oxobutanoic acid
2-benzyl-4-(3,4-methylenedioxyphenyl)-4-oxobutanoic acid
2-benzyl-4-cyclohexyl-4-oxobutanoic acid
4-phenyl-2-[(tetrahydrofur-2-yl)methyl]4-oxobutanoic acid,
the solvates, enantiomers and salts of these acids.

Advantageously, the 4-oxobutanoic acid derivative is chosen from:
(−)-2-benzyl-4-(4-methoxyphenyl)-4-oxobutanoic acid
(+)-2-benzyl-4-(4-methoxyphenyl)-4-oxobutanoic acid
(−)-2-benzyl-4-(4-fluorophenyl)-4-oxobutanoic acid
(+)-2-benzyl-4-(4-fluorophenyl)-4-oxobutanoic acid,
the solvates and salts of these acids.

The compound that is most particularly preferred is 2-benzyl-4-(4-fluorophenyl)-4-oxobutanoic acid, its solvates, its enantiomers and its salts.

The compounds of the formula (I) were subjected to biological tests designed to reveal their anti-inflammatory activity. The in vivo activity of the compounds of the formula (I) was studied in an experimental model of inflammation in rats. Inflammatory oedema of the rat paw is induced by intradermal injection of carrageenan (1% V/V) into the hind paw of the rat. This oedema is measured by plethysmometry according to the method of Winter C. A. et al. (Proc. Soc. Exp. Biol. Med.; (1962); 111; 544-547). The substances with an anti-inflammatory effect bring about a reduction in the oedema thus created. Indomethacin is used as anti-inflammatory reference in the test.

The results show that the compounds of the formula (I) have anti-inflammatory properties in vivo. The treatment of inflammation may be performed preventively or curatively.

They may thus be used in this respect in the symptomatic treatment of painful conditions of mild to moderate intensity and/or febrile conditions, more particularly in diabetic neuropathy, polyarthritis, arthrosis, lumbago, traumato-logical pain and ORL inflammations.

The inflammation treated according to the invention may be associated with pathologies of insulin-resistant metabolic syndrome, with pathologies resulting from diabetes, for instance retinopathy, nephropathy, neuropathy, micro- and macro-angiopathy, hypertension or atherosclerosis. Specifically, diabetic patients with poor glycaemic control are liable to develop atherosclerotic plaque infections associated with an inflammatory process [Endocr.; 2000, 6(3), 272-276]. This inflammation may also be associated with pathologies of central origin, for instance neurodegenerative diseases such as, especially, Alzheimer's disease or Parkinson's disease [Lancet; 2001, Aug. 11, 358 (9280), 436—J. Neuropathol. Exp. Neurol. 2001; Oct.; 60 (10); 923].

The compounds of the invention may be presented, in combination with any suitable excipient, in any form that is suitable for enteral (more particularly oral) or parenteral administration, for example in the form of tablets, gel capsules, powders, sugar-coated tablets, or drinkable or injectable solutions. These suitable forms and suitable excipients are as defined in patent application WO 98/7681 filed by the Applicant.

The compounds of the formula (I) may be administered in daily doses of between about 1 and 400 mg to adults orally, or between 0.1 and 200 mg parenterally.

The examples below illustrate the present invention without, however, limiting it.

EXAMPLES

Experimental data:
Animal model: Rat of Wistar type
Anti-inflammatory reference: indomethacin from the company Sigma
Control: 0.5% methylcellulose hydrogel.

After fasting for one day, the volume of the right hind paw is measured [V paw]. The test compounds, the reference and the control are administered orally in a volume of 10 ml/kg. One hour after administration, oedema is induced by an intraplantar injection of 50 microliters of carrageenan (1%, VN) hydrogel into the right hind paw. The volume of this paw is measured three hours after inducing the oedema. The intensity of the oedema [V oedema] is evaluated by the difference in the volume of the paw, before and three hours after the injection of carrageenan.

The results are collated in the table below:

| TEST OF CARRAGEENAN-INDUCED INFLAMMATORY OEDEMA | | | |
| --- | --- | --- | --- |
| | V paw (ml) | V oedema (ml) | Reduction in oedema (%) |
| Controls | 1.65 | 0.62 | — |
| Indomethacin | 1.65 | 0.20 | −67 |
| P (30 mg) | 1.57 | 0.42 | −32 |
| P (100 mg) | 1.67 | 0.11 | −83 |
| P (300 mg) | 1.71 | 0.17 | −73 |

P corresponds to (−)-2-benzyl-4-(4-fluorophenyl)-4-oxobutanoic acid.

The experimental results show the anti-inflammatory effect of the compounds corresponding to the general formula (I).

The invention claimed is:

1. A method for treating inflammation, which inflammation is diabetic neuropathy, polyarthritis, arthrosis, lumbago, traumatological pain, oto-rhino-laryngological inflammation, inflammation associated with pathologies of insulin-resistant metabolic syndrome, or inflammation associated with pathologies resulting from diabetes, nephropathy, hypertension or atherosclerosis, comprising administering to a subject in need thereof an effective amount of one of the following compounds
   2-benzyl-4-(4-methoxyphenyl)-4-oxobutanoic acid;
   2-benzyl-4-(4-fluorophenyl)-4-oxobutanoic acid;
   2-cyclohexylmethyl-4-(4-methoxyphenyl)-4-oxobutanoic acid;
   2-benzyl-4-phenyl-4-oxobutanoic acid;
   2-(β-naphthylmethyl)-4-phenyl-4-oxobutanoic acid;
   2-benzyl-4-(β-naphthyl)-4-oxobutanoic acid;
   2-[(4-chlorophenyl)methyl]-4-(4-methoxyphenyl)-4-oxobutanoic acid;
   2-benzyl-4-(4-methylphenyl)-4-oxobutanoic acid;
   4-(4-fluorophenyl)-2-[(4-methoxyphenyl)methyl]-4-oxobutanoic acid;
   2-benzyl-4-(3,4-methylenedioxyphenyl)-4-oxobutanoic acid;
   2-benzyl-4-cyclohexyl-4-oxobutanoic acid; or
   4-phenyl-2-[(tetrahydrofur-2-yl)methyl]-4-oxobutanoic acid;
   or a salt thereof.

2. A method according to claim 1, wherein one of the following compounds is administered
   (−)-2-benzyl-4-(4-methoxyphenyl)-4-oxobutanoic acid;
   (+)-2-benzyl-4-(4-methoxyphenyl)-4-oxobutanoic acid;
   (−)-2-benzyl-4-(4-fluorophenyl)-4-oxobutanoic acid; or
   (+)-2-benzyl-4-(4-fluorophenyl)-4-oxobutanoic acid;
   or a salt thereof.

3. The method according to claim 1, wherein one of the following compounds is administered
   2-benzyl-4-(4-methoxyphenyl)-4-oxobutanoic acid;
   2-benzyl-4-(4-fluorophenyl)-4-oxobutanoic acid;
   2-cyclohexylmethyl-4-(4-methoxyphenyl)-4-oxobutanoic acid;
   2-benzyl-4-phenyl-4-oxobutanoic acid;
   2-(β-naphthylmethyl)-4-phenyl-4-oxobutanoic acid;
   2-benzyl-4-(β-naphthyl)-4-oxobutanoic acid;
   2-[(4-chlorophenyl)methyl]-4-(4-methoxyphenyl)-4-oxobutanoic acid;
   2-benzyl-4-(4-methylphenyl)-4-oxobutanoic acid;
   4-(4-fluorophenyl)-2-[(4-methoxyphenyl)methyl]-4-oxobutanoic acid;
   2-benzyl-4-(3,4-methylenedioxyphenyl)-4-oxobutanoic acid;
   2-benzyl-4-cyclohexyl-4-oxobutanoic acid; or 4-phenyl-2-[(tetrahydrofur-2-yl)methyl]-4-oxobutanoic acid.

4. The method according to claim 2, wherein one of the following compounds is administered
   (−)-2-benzyl-4-(4-methoxyphenyl)-4-oxobutanoic acid;
   (+)-2-benzyl-4-(4-methoxyphenyl)-4-oxobutanoic acid;
   (−)-2-benzyl-4-(4-fluorophenyl)-4-oxobutanoic acid; or
   (+)-2-benzyl-4-(4-fluorophenyl)-4-oxobutanoic acid.

5. The method according to claim 3, wherein the treatment is for treating diabetic neuropathy, polyarthritis, arthrosis, lumbago, traumatological pain or oto-rhino-laryngological inflammation.

6. The method according to claim 3, wherein the treatment is for treating inflammation associated with pathologies of insulin-resistant metabolic syndrome.

7. The method according to claim 3, wherein the treatment is for treating inflammation associated with pathologies resulting from diabetes, nephropathy, hypertension or atherosclerosis.

8. The method according to claim 1, wherein an enantiomer of one of the compounds is administered.

9. The method according to claim 1, wherein a salt of one of the following compounds is administered
   2-benzyl-4-(4-methoxyphenyl)-4-oxobutanoic acid;
   2-benzyl-4-(4-fluorophenyl)-4-oxobutanoic acid;
   2-cyclohexylmethyl-4-(4-methoxyphenyl)-4-oxobutanoic acid;
   2-benzyl-4-phenyl-4-oxobutanoic acid;
   2-(β-naphthylmethyl)-4-phenyl-4-oxobutanoic acid;
   2-benzyl-4-(β-naphthyl)-4-oxobutanoic acid;
   2-[(4-chlorophenyl)methyl]-4-(4-methoxyphenyl)-4-oxobutanoic acid;
   2-benzyl-4-(4-methylphenyl)-4-oxobutanoic acid;

4-(4-fluorophenyl)-2-[(4-methoxyphenyl)methyl]-4-oxobutanoic acid;

2-benzyl-4-(3,4-methylenedioxyphenyl)-4-oxobutanoic acid;

2-benzyl-4-cyclohexyl-4-oxobutanoic acid; or 4-phenyl-2-[(tetrahydrofur-2-yl)methyl]-4-oxobutanoic acid.

10. The method according to claim 2, wherein a salt of one of the following compounds is administered (−)-2-benzyl-4-(4-methoxyphenyl)-4-oxobutanoic acid;

(+)-2-benzyl-4-(4-methoxyphenyl)-4-oxobutanoic acid;

(−)-2-benzyl-4-(4-fluorophenyl)-4-oxobutanoic acid; or (+)-2-benzyl-4-(4-fluorophenyl)-4-oxobutanoic acid.

11. The method according to claim 1, wherein (−)-2-benzyl-4-(4-fluorophenyl)-4-oxobutanoic acid is administered.

12. The method according to claim 1, wherein a salt of (−)-2-benzyl-4-(4-fluorophenyl)-4-oxobutanoic acid is administered.

* * * * *